(12) United States Patent
Teetzel et al.

(10) Patent No.: US 8,950,401 B2
(45) Date of Patent: Feb. 10, 2015

(54) SELF-CONTAINED BREATHING SYSTEM

(75) Inventors: James W. Teetzel, York, ME (US); Gary M. Lemire, Lee, NH (US); Daniel A. Desrosiers, Epping, NH (US); Mark A. Hansen, Virginia Beach, VA (US)

(73) Assignee: Wilcox Industries Corp., Newington, NH (US)

( * ) Notice: Subject to any disclaimer, the term of this patent is extended or adjusted under 35 U.S.C. 154(b) by 78 days.

(21) Appl. No.: 13/371,744

(22) Filed: Feb. 13, 2012

(65) Prior Publication Data

US 2012/0138059 A1    Jun. 7, 2012

Related U.S. Application Data

(63) Continuation of application No. 12/688,676, filed on Jan. 15, 2010, now Pat. No. 8,113,198, which is a continuation of application No. 10/924,281, filed on Aug. 23, 2004, now Pat. No. 7,647,927.

(60) Provisional application No. 60/497,215, filed on Aug. 23, 2003, provisional application No. 60/497,206, filed on Aug. 22, 2003.

(51) Int. Cl.
| | | |
|---|---|---|
| *B01D 19/00* | (2006.01) | |
| *B01D 59/50* | (2006.01) | |
| *B01D 59/26* | (2006.01) | |

(Continued)

(52) U.S. Cl.
CPC ... *A62B 7/10* (2013.01); *A62B 9/04* (2013.01); *A62B 18/006* (2013.01); *A62B 18/10* (2013.01)
USPC ............ 128/205.12; 55/467; 55/471; 55/472; 55/473; 55/484; 95/90.01; 95/273; 96/108; 96/121; 96/133; 96/142; 128/204.18; 128/205.23; 128/205.28

(58) Field of Classification Search
USPC ............ 128/205.12, 205.23, 205.28, 204.18; 95/90.01, 273; 96/108, 121, 133, 142; 55/467, 471, 472, 473, 484
See application file for complete search history.

(56) References Cited

U.S. PATENT DOCUMENTS

| | | |
|---|---|---|
| 2,085,249 A | 6/1937 | Bullard |
| 2,284,054 A | 5/1942 | Siegwart |

(Continued)

FOREIGN PATENT DOCUMENTS

| | | |
|---|---|---|
| DE | 19503027 | 3/1996 |
| DE | 3512644 | 10/2006 |

(Continued)

OTHER PUBLICATIONS

SCOUT System (Self Contained Operational Utility Tank) brochure, Order No. 20000G01, Wilcox Industries Corp., 2002, 2 pages.

(Continued)

*Primary Examiner* — Victoria J Hicks
*Assistant Examiner* — Brandon L Jackson
(74) *Attorney, Agent, or Firm* — McLane, Graf, Raulerson & Middleton, Professional Association

(57) ABSTRACT

A breathing apparatus is operable in self-contained and filtered modes of operation. In the self-contained mode of operation, a breathable gas is delivered to a user from a self-contained source of breathing gas. In a second, filtered mode of operation, a suction source draws ambient air through a filter removing contaminants and delivers filtered ambient air to the user. A method of delivering air to a subject is also provided.

16 Claims, 16 Drawing Sheets

(51) Int. Cl.

| | |
|---|---|
| *B01D 46/00* | (2006.01) |
| *A61M 16/00* | (2006.01) |
| *A62B 7/00* | (2006.01) |
| *A62B 7/10* | (2006.01) |
| *A62B 1/00* | (2006.01) |
| *A62B 9/04* | (2006.01) |
| *A62B 18/00* | (2006.01) |
| *A62B 18/10* | (2006.01) |

(56) References Cited

U.S. PATENT DOCUMENTS

| | | | |
|---|---|---|---|
| 2,284,249 A | 5/1942 | Siegwart | |
| 2,450,446 A | 10/1948 | Rupp | |
| 2,484,217 A | 10/1949 | Gardenier | |
| 2,787,782 A | 4/1957 | Rosenblum et al. | |
| 2,817,350 A | 12/1957 | Bradner et al. | |
| 2,818,860 A | 1/1958 | Holm et al. | |
| 2,828,741 A | 4/1958 | Delest | |
| 2,998,009 A | 8/1961 | Holm et al. | |
| 3,000,805 A | 9/1961 | Carritt et al. | |
| 3,092,104 A | 6/1963 | Cassidy | |
| 3,106,205 A | 10/1963 | Balshaw | |
| 3,202,150 A | 8/1965 | Miller | |
| 3,250,873 A | 5/1966 | Kudlaty et al. | |
| 3,252,458 A * | 5/1966 | Krasberg | 128/204.22 |
| 3,410,778 A | 11/1968 | Krasberg | |
| 3,456,642 A | 7/1969 | Cupp | |
| 3,508,542 A | 4/1970 | Browner | |
| 3,556,098 A | 1/1971 | Kanwisher et al. | |
| 3,587,438 A | 6/1971 | Foster et al. | |
| 3,739,774 A * | 6/1973 | Gregory | 128/201.28 |
| 3,773,044 A | 11/1973 | Wallace | |
| 3,805,590 A | 4/1974 | Ringwall et al. | |
| 3,896,837 A | 7/1975 | Rohling | |
| 3,911,413 A | 10/1975 | Wallace | |
| 3,957,044 A | 5/1976 | Fletcher et al. | |
| 4,121,578 A | 10/1978 | Torzala | |
| 4,127,122 A | 11/1978 | Kienhofer et al. | |
| 4,146,887 A | 3/1979 | Magnante | |
| 4,250,876 A | 2/1981 | Kranz | |
| 4,273,120 A | 6/1981 | Oswell | |
| 4,417,575 A | 11/1983 | Hilton et al. | |
| 4,419,994 A | 12/1983 | Hilton | |
| 4,423,723 A | 1/1984 | Winkler et al. | |
| 4,430,995 A | 2/1984 | Hilton | |
| 4,440,162 A | 4/1984 | Sewell et al. | |
| 4,463,755 A | 8/1984 | Suzuki | |
| 4,510,193 A | 4/1985 | Blucher et al. | |
| 4,567,889 A | 2/1986 | Lehmann | |
| 4,572,323 A | 2/1986 | Randall | |
| 4,590,951 A | 5/1986 | O'Connor | |
| 4,612,239 A | 9/1986 | Dimanshteyn | |
| 4,633,868 A | 1/1987 | Itoh et al. | |
| 4,676,236 A | 6/1987 | Piorkowski et al. | |
| D295,046 S | 4/1988 | Odell | |
| 4,741,332 A | 5/1988 | Beaussant | |
| 4,873,970 A | 10/1989 | Freidank et al. | |
| 4,887,638 A | 12/1989 | Hellquist et al. | |
| 4,899,740 A | 2/1990 | Napolitano | |
| 4,905,683 A | 3/1990 | Cronjaeger | |
| 4,926,855 A | 5/1990 | Hellquist et al. | |
| 4,971,052 A | 11/1990 | Edwards | |
| 5,018,518 A | 5/1991 | Hubner | |
| 5,035,239 A | 7/1991 | Edwards | |
| 5,080,414 A | 1/1992 | Hellquist et al. | |
| 5,097,826 A | 3/1992 | Gray et al. | |
| 5,112,666 A | 5/1992 | Langston | |
| 5,115,804 A | 5/1992 | Brookman | |
| 5,221,572 A | 6/1993 | Meunier | |
| 5,265,592 A | 11/1993 | Beaussant | |
| 5,322,058 A | 6/1994 | Pasternack | |
| 5,323,774 A | 6/1994 | Fehlauer | |
| 5,370,112 A | 12/1994 | Perkins | |
| 5,392,773 A * | 2/1995 | Bertrand | 128/206.11 |
| 5,413,097 A | 5/1995 | Birenheide et al. | |
| 5,562,092 A | 10/1996 | George | |
| 5,577,496 A | 11/1996 | Blackwood et al. | |
| 5,584,286 A | 12/1996 | Kippax | |
| 5,626,947 A | 5/1997 | Hauer et al. | |
| 5,666,949 A | 9/1997 | Debe et al. | |
| 5,685,296 A * | 11/1997 | Zdrojkowski et al. | 128/205.24 |
| 5,743,775 A | 4/1998 | Baurmeister | |
| 5,758,641 A | 6/1998 | Karr | |
| 5,832,916 A | 11/1998 | Lundberg | |
| 5,848,591 A | 12/1998 | Weismann | |
| 5,901,705 A * | 5/1999 | Leagre | 128/207.14 |
| 5,906,203 A | 5/1999 | Klockseth et al. | |
| 5,915,834 A | 6/1999 | McCulloh | |
| 5,950,621 A | 9/1999 | Klockseth et al. | |
| 5,964,218 A | 10/1999 | Smith et al. | |
| 6,102,034 A | 8/2000 | Buhlmann | |
| 6,105,632 A | 8/2000 | Buhlmann | |
| 6,167,882 B1 | 1/2001 | Almqvist et al. | |
| 6,186,140 B1 | 2/2001 | Hoague | |
| 6,290,111 B1 | 9/2001 | Hedenberg et al. | |
| 6,328,031 B1 | 12/2001 | Tischer et al. | |
| 6,349,721 B1 | 2/2002 | Grilliot et al. | |
| 6,360,742 B1 * | 3/2002 | Maxwell et al. | 128/202.27 |
| 6,401,714 B1 * | 6/2002 | Giorgini | 128/204.26 |
| 6,553,989 B1 | 4/2003 | Richardson et al. | |
| 6,575,165 B1 | 6/2003 | Cook et al. | |
| 6,895,960 B2 | 5/2005 | Fabin | |
| 6,957,653 B2 | 10/2005 | Campbell et al. | |
| 6,978,782 B2 | 12/2005 | Tayebi | |
| 7,380,551 B2 * | 6/2008 | Alvey | 128/201.25 |
| 7,543,584 B2 | 6/2009 | Brookman | |
| 7,647,927 B2 * | 1/2010 | Teetzel et al. | 128/205.12 |
| 8,113,198 B2 | 2/2012 | Teetzel et al. | |
| 2002/0069876 A1 * | 6/2002 | Loser et al. | 128/203.19 |
| 2002/0092522 A1 | 7/2002 | Fabin | |
| 2004/0040561 A1 | 3/2004 | Tayebi | |
| 2004/0182394 A1 | 9/2004 | Alvey et al. | |
| 2004/0182395 A1 | 9/2004 | Brookman | |
| 2005/0022817 A1 | 2/2005 | Alvey | |
| 2005/0103335 A1 | 5/2005 | Fabin | |
| 2005/0109341 A1 | 5/2005 | Alvey | |
| 2006/0048777 A1 | 3/2006 | Brookman | |
| 2006/0191533 A1 | 8/2006 | Brookman et al. | |

FOREIGN PATENT DOCUMENTS

| | | |
|---|---|---|
| EP | 0094757 | 11/1983 |
| EP | 0241188 | 10/1987 |
| FR | 814750 | 6/1937 |
| FR | 886782 | 10/1943 |
| FR | 2514934 | 10/1981 |
| GB | 2025316 | 1/1980 |
| GB | 1587812 | 4/1981 |
| WO | WO00/57738 | 10/2000 |
| WO | WO01/32266 | 5/2001 |

OTHER PUBLICATIONS

Wilcox Industries Corp. Invoice No. 2328-0104-00 and Packing List, dated Dec. 31, 2002, 2 pages.
Scott Health & Safety, Air-Pak Fifty SCBA, Brochure No. H/S 5807 I (Feb. 2004).
Scott Health & Safety, C420 PPR, Brochure No. H/S 6171 B (Aug. 2001).
Facsimile correspondence sent to the U.S. Navel Inventory Control Point, Dave Duval, from Wilcox Industries Corp., Robert F. Guarasi, dated Aug. 23, 2002, 10 pages.

\* cited by examiner

SELF-CONTAINED BREATHING SYSTEM

CROSS-REFERENCE TO RELATED APPLICATIONS

This application claims priority as a continuation application under 35 U.S.C. §120 to U.S. patent application Ser. No. 12/688,676, filed Jan. 15, 2010, now U.S. Pat. No. 8,113,198, which claims priority as a continuation application under 35 U.S.C. §120 to U.S. patent application Ser. No. 10/924,281, filed Aug. 23, 2004, now U.S. Pat. No. 7,647,927, which claims the benefit under 35 U.S.C. §119(e) of U.S. provisional application Ser. No. 60/497,206 filed Aug. 22, 2003, and U.S. provisional application Ser. No. 60/497,215 filed Aug. 23, 2003. Each of the aforementioned applications is incorporated herein by reference in its entirety.

FIELD OF THE INVENTION

The present invention relates to a breathing system and, more particularly, a dual-purpose, self-contained breathing system in which the air source is switchable between self-contained air supply and filtered ambient air, as required by the operator. The system finds utility in connection with all manner of hazardous or contaminated environments in which a self-contained breathing apparatus (SCBA) is required, including, chemical, biological, and radiological environments, burning buildings, and so forth. The system allows the user to switch between a self-contained air supply and filtered ambient air without the need to switch hoses, thereby reducing potential exposure to contaminants in a hazardous, contaminated, or toxic environment.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
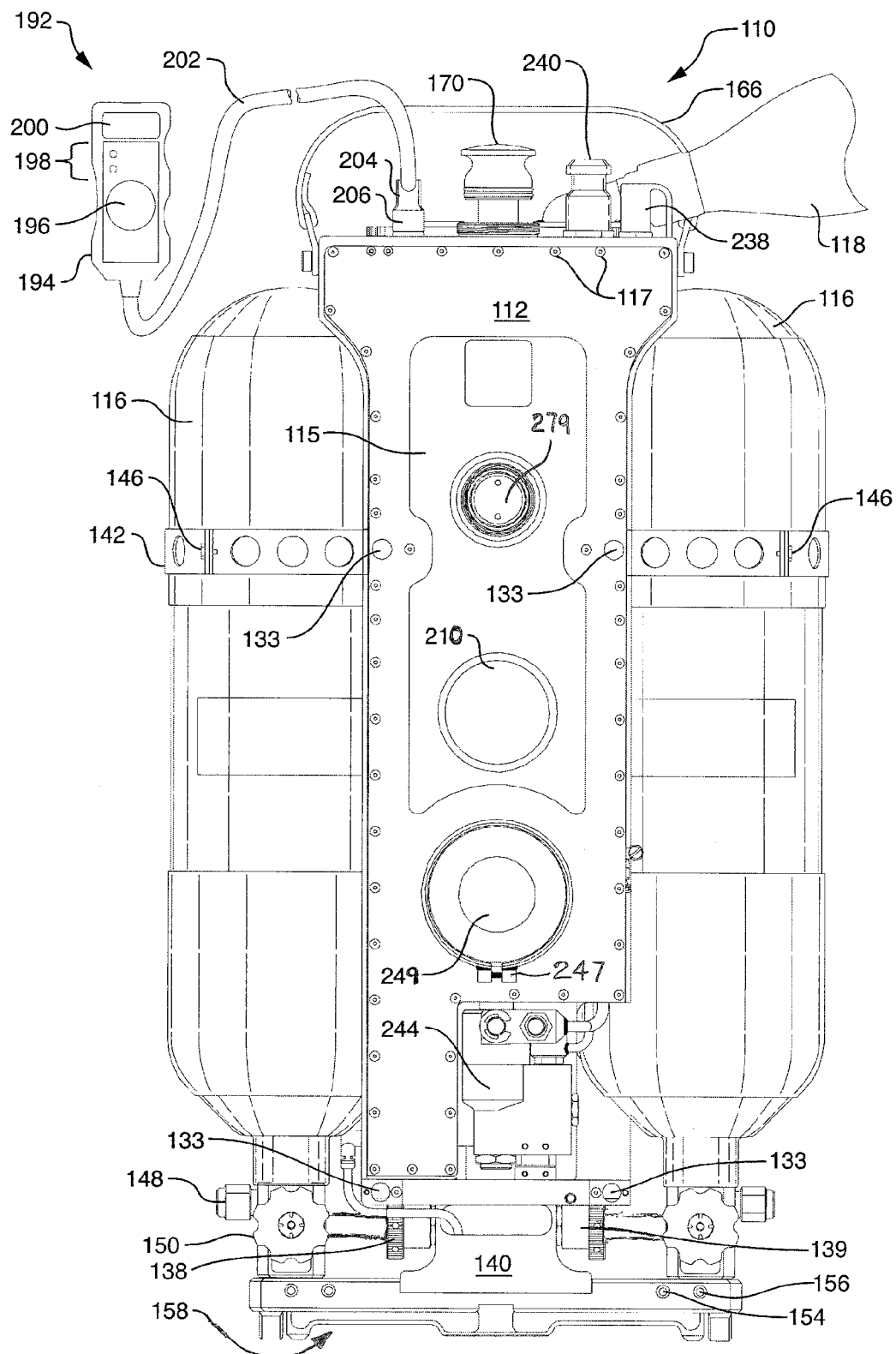
FIG. 1 is a front elevational view of an exemplary breathing apparatus according to the present invention.
Figure 2:
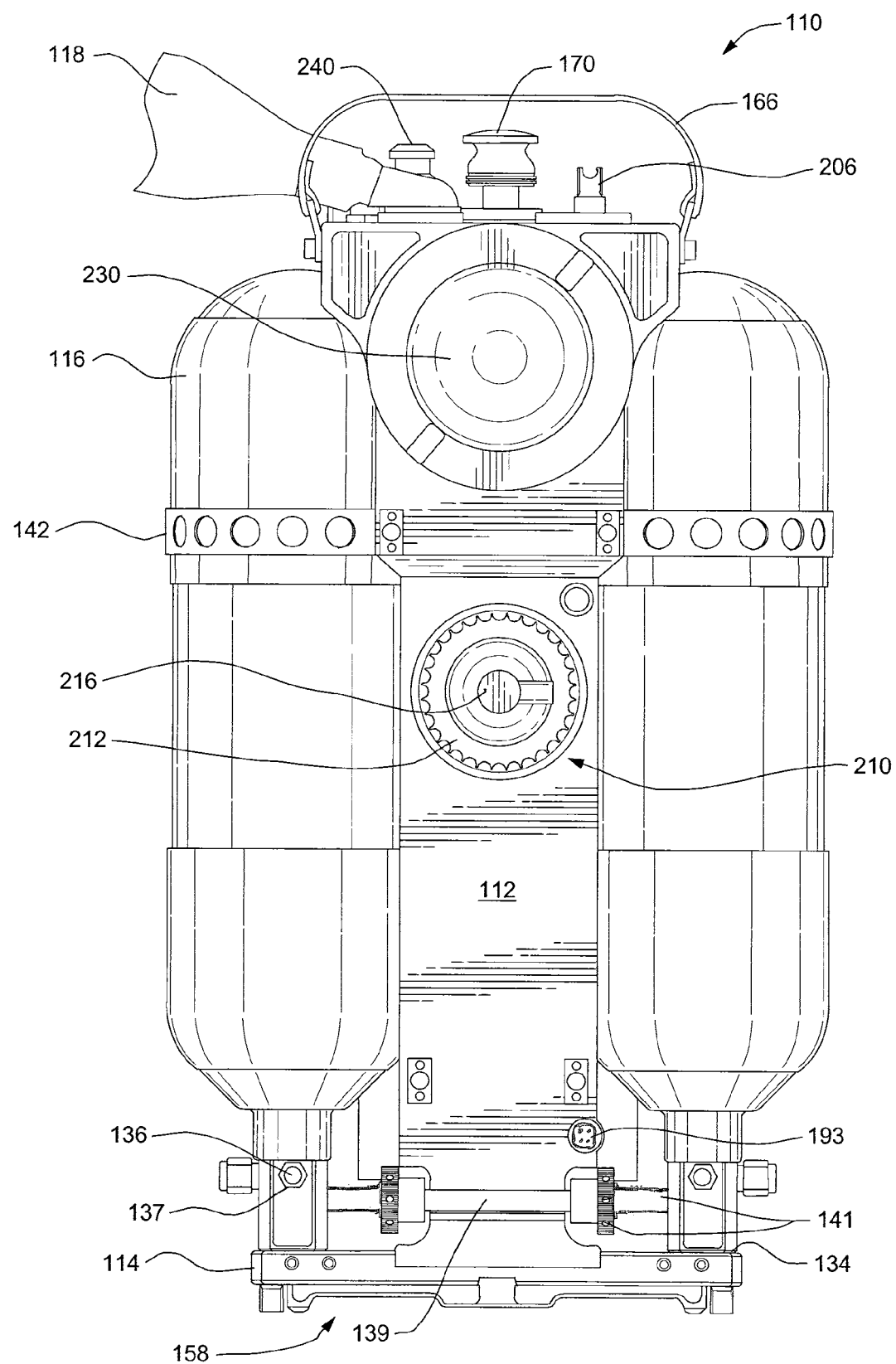
FIG. 2 is a rear elevational view of the breathing apparatus shown in FIG. 1.

Referring now to the drawing figures, wherein the showings are for purposes of illustrating preferred embodiments of the invention only and not for limiting the same, FIGS. 1-10 illustrate a breathing apparatus 110 including a main body or housing section 112, a base manifold section 114, one or more self-contained air supply tanks 116, and a breathing hose 118. The hose 118 includes a first end 120 which may be attached to an outlet port 122 on the housing 112. A second end 124 may be attached to an inlet port 129 of a face mask 126 worn by a user 128 for delivery of breathable air. The mask assembly 126 may be of a type commonly used in chemical, biological, radiological, or other hazardous environments.

Figure 3:
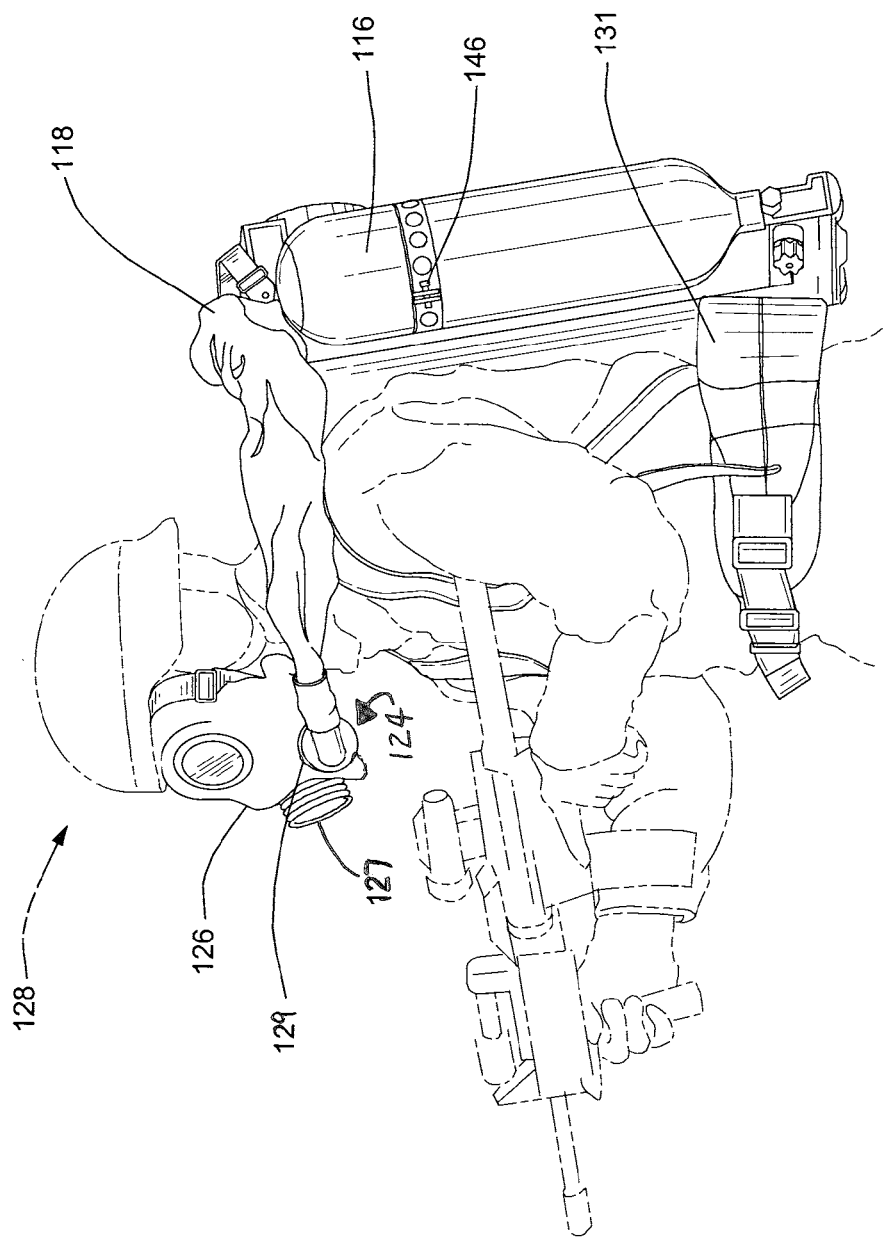
FIG. 3 is an exemplary embodiment of a breathing apparatus according to the present invention adapted to be worn by a user.
Figure 4:
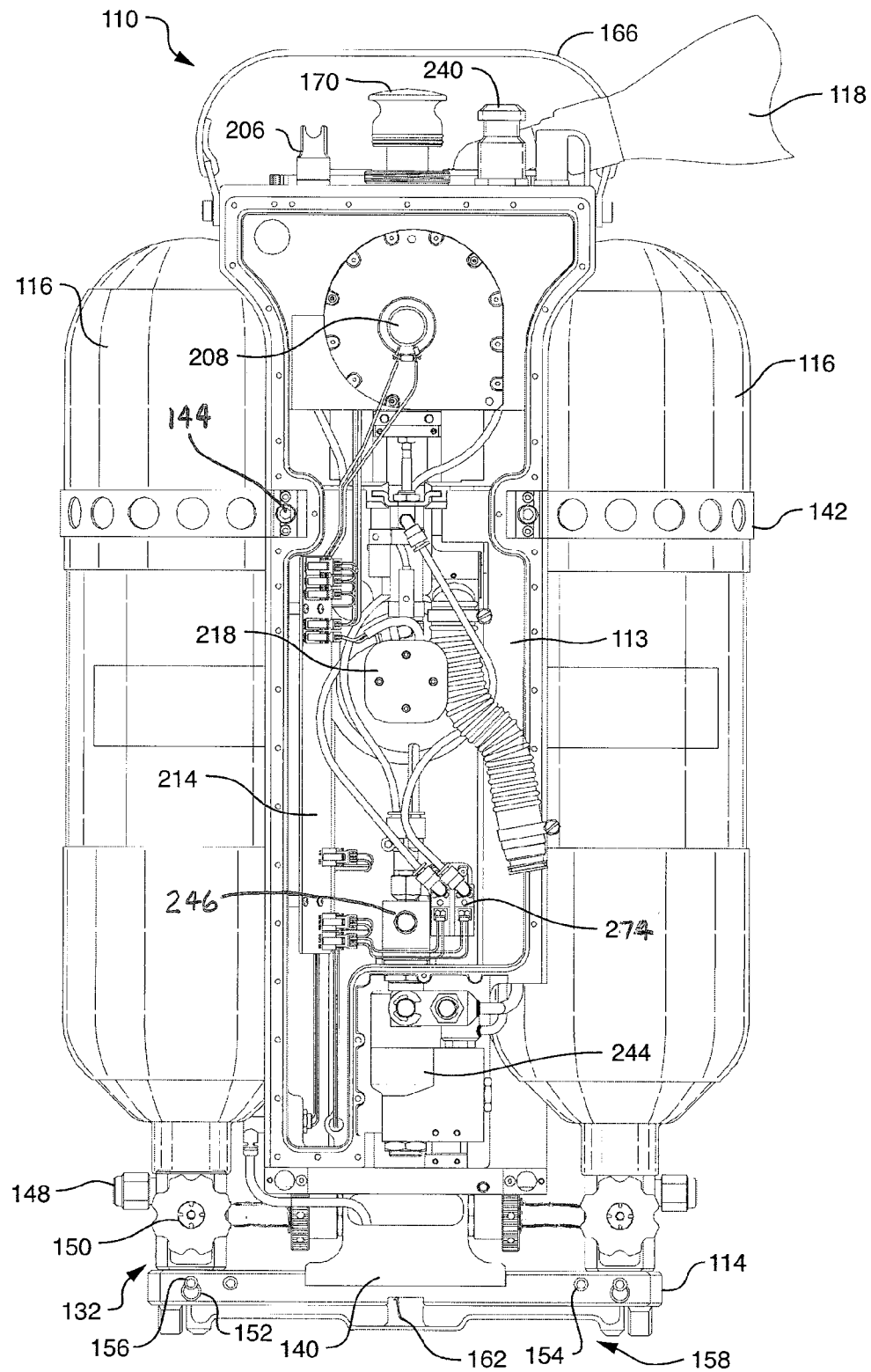
FIG. 4 is a front elevational view of the breathing apparatus shown in FIG. 1 with the housing cover removed.
Figure 5:
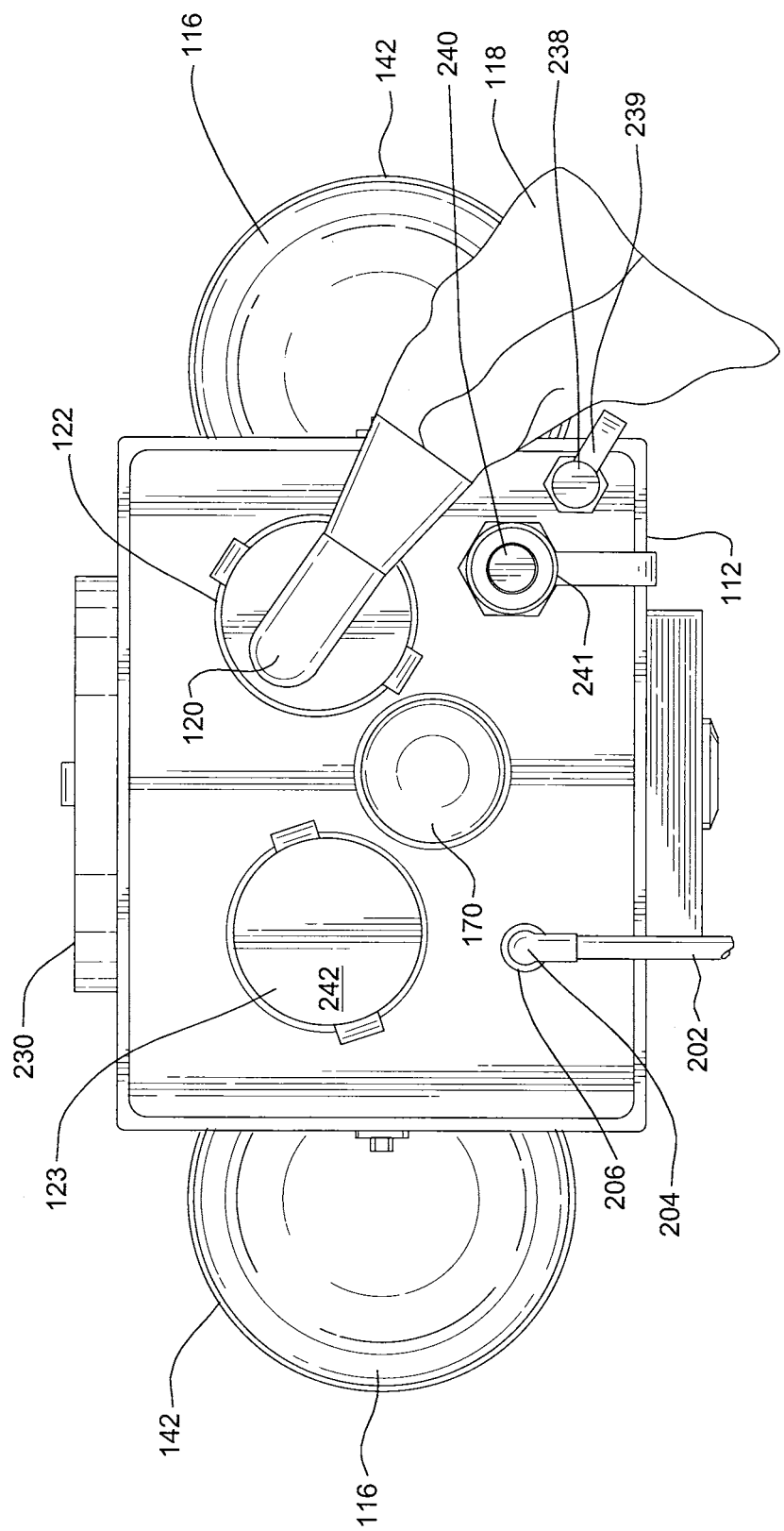
FIG. 5 is a top plan view of the breathing apparatus shown in FIG. 1.

A plurality of fasteners such as connecting pins 133 or other fasteners may be provided on the exterior of the housing 112 to secure the unit 110 to a user wearable garment 131, such as a ballistic vest, emergency ditch system, or the like (see FIG. 3).

In operation, the breathing device 110 is switchable between a first, pressurized air mode in which air from the pressurized tanks 116 is delivered to the user 128 via the air hose 118 and a second, filtration mode in which ambient air is filtered via a filtration unit (as described below) and is likewise delivered to the user 128 via the hose 118. In this manner the operator 128 has the ability to readily select the desired mode of operation, namely, a SCBA mode in which air is delivered from an attached cylinder 116 and powered air-purifying respirator (PAPR) mode of operation in which filtered ambient air is drawn with blower assistance through one or more air filters or purifiers and delivered to the user. The facile switching between the self-contained air supply 116 and filtered air is particularly advantageous, for example, in the event that the self-contained air supply 116 becomes exhausted or malfunctions, when it is desired to conserve the self-contained air supply, and so forth. Likewise, a user operating on filtered air may readily switch to the self-contained air supply, for example, in low oxygen conditions or when the ambient air contains dangerous levels of a non-filterable constituent, e.g., as may be detected employing an optional air sampler module, as described in further detail below.

The main chassis 112 defines an internal cavity or compartment 113, and may be manufactured of plastic, preferably chemically hardened plastic, composite materials, aluminum or other metal and alloys thereof, or the like. The main chassis 112 provides for mounting of externally mounted components thereon and the internal cavity 113 contains internal components, such as a power supply 218, a circuit board 214 and associated circuitry, blower 208, internal filter 222, and other interior components, for operation of the apparatus 110.

Figure 8:
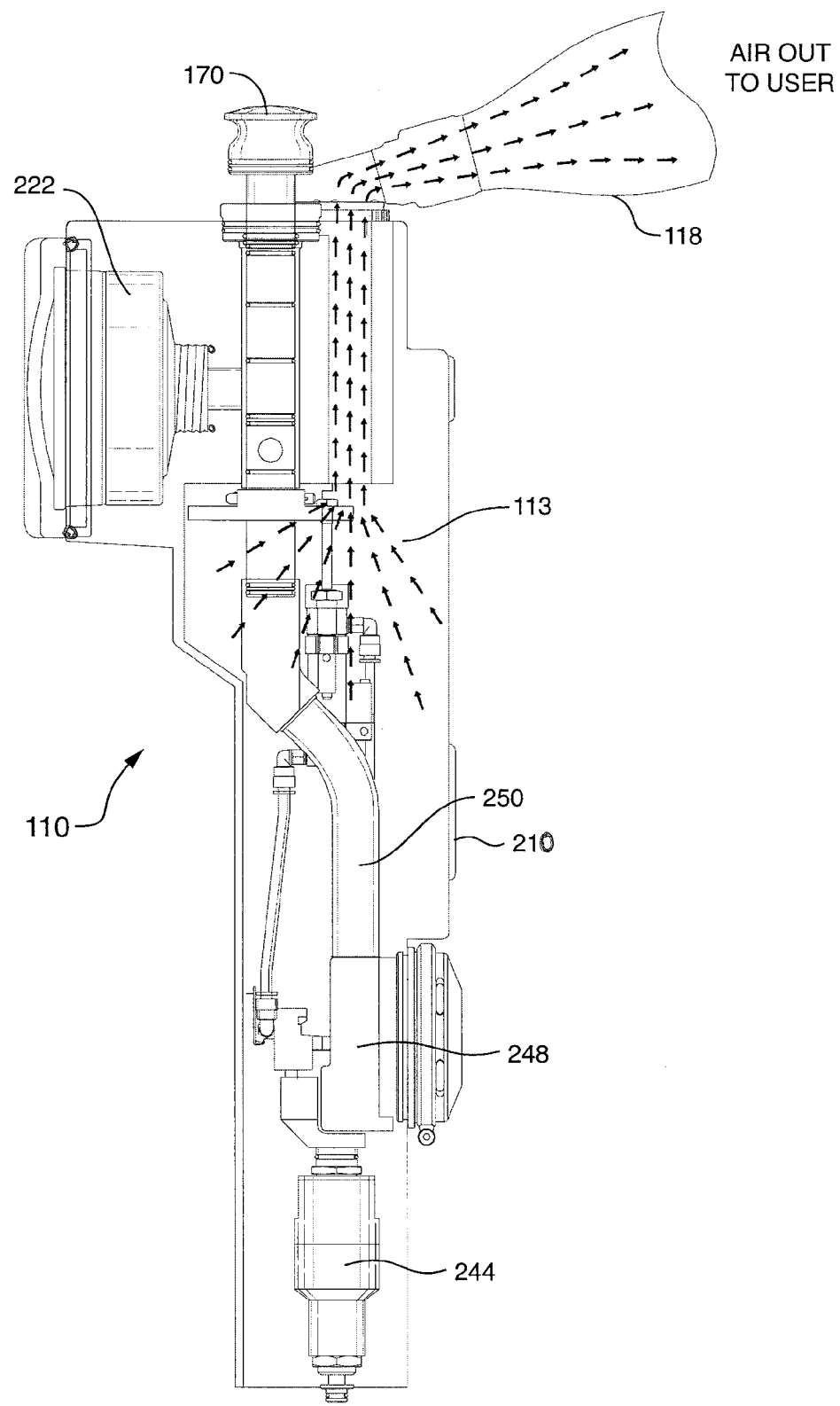
FIGS. 8-10 are side sectional views illustrating the flow of air through the breathing apparatus.
Figure 9:
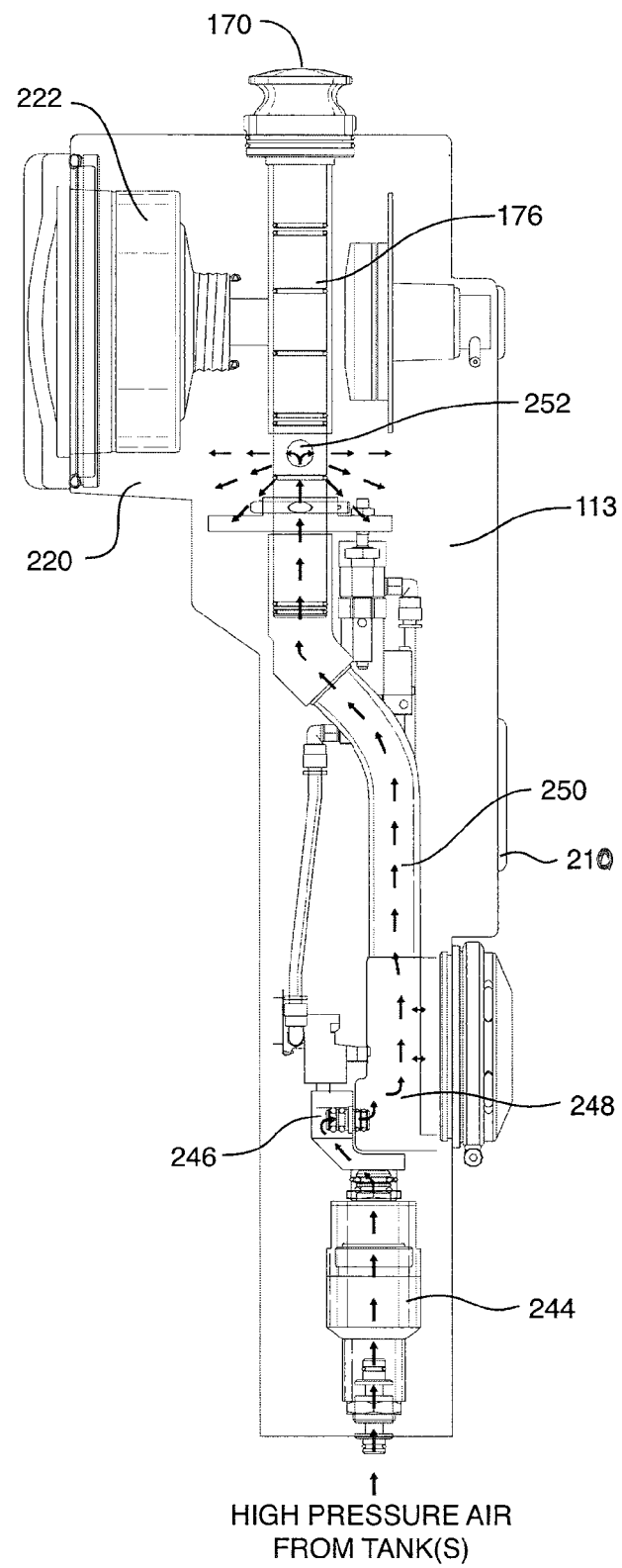
Figure 10:
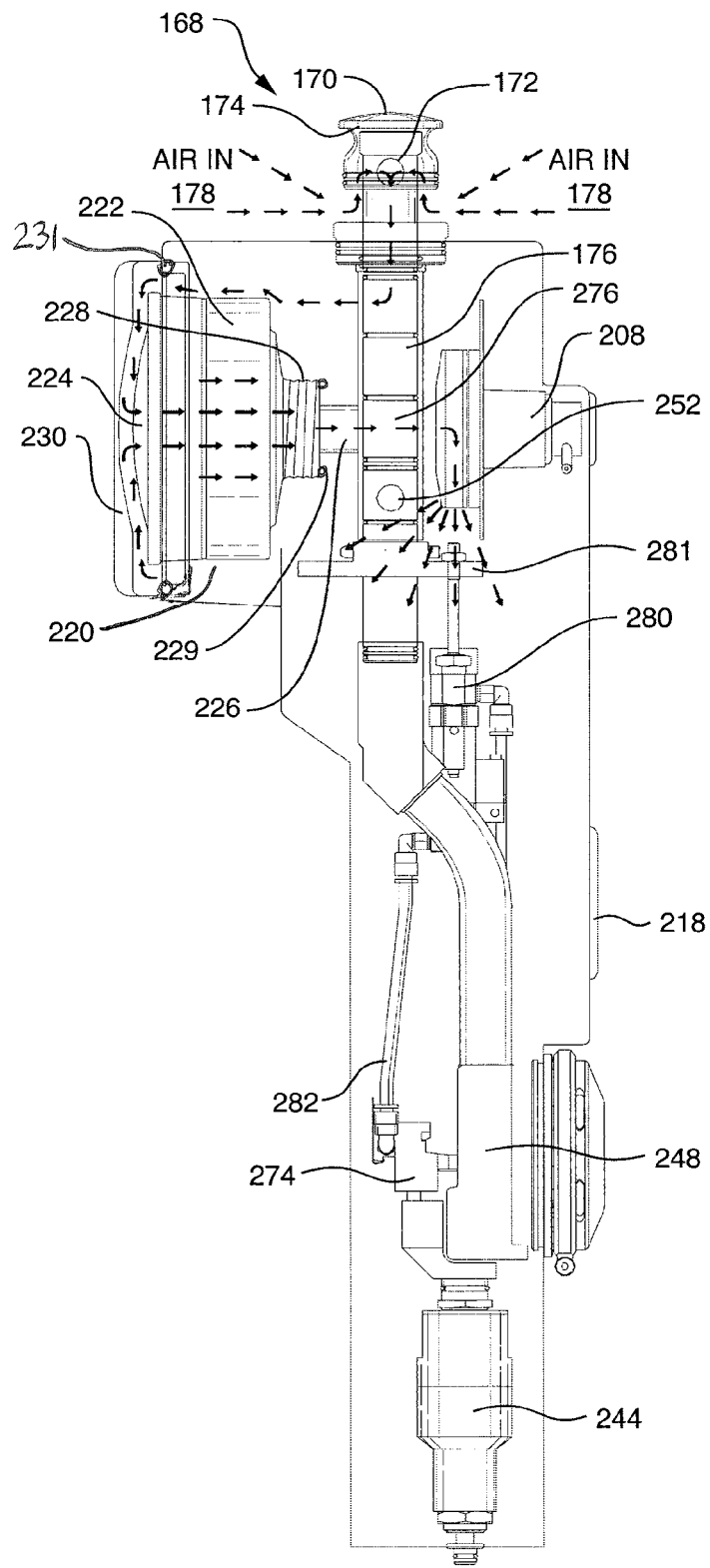

In the depicted embodiment, the cavity 113 also serves as the main breathing reservoir. As best seen in FIG. 8, the breathing reservoir 113 is in flow communication with the breathing hose 118. The housing 112 and all connectors and access ports thereon are sealed against entry of external environmental contamination, thereby allowing the unit to be employed underwater or in otherwise wet or damp conditions. The breathing gas (either gas from tank 116 or purified ambient air) is allowed to fill the chamber 113 and breathing bag 118 to provide additional "next breath" capability and the positive pressure within the breathing chamber 113, in turn, provides additional resistance against ingress of moisture or other external contaminants. However, it will be recognized that alternative embodiments wherein the flow is confined to a conduit or more limited passageway within the chassis 112 are also contemplated.

Figure 15:
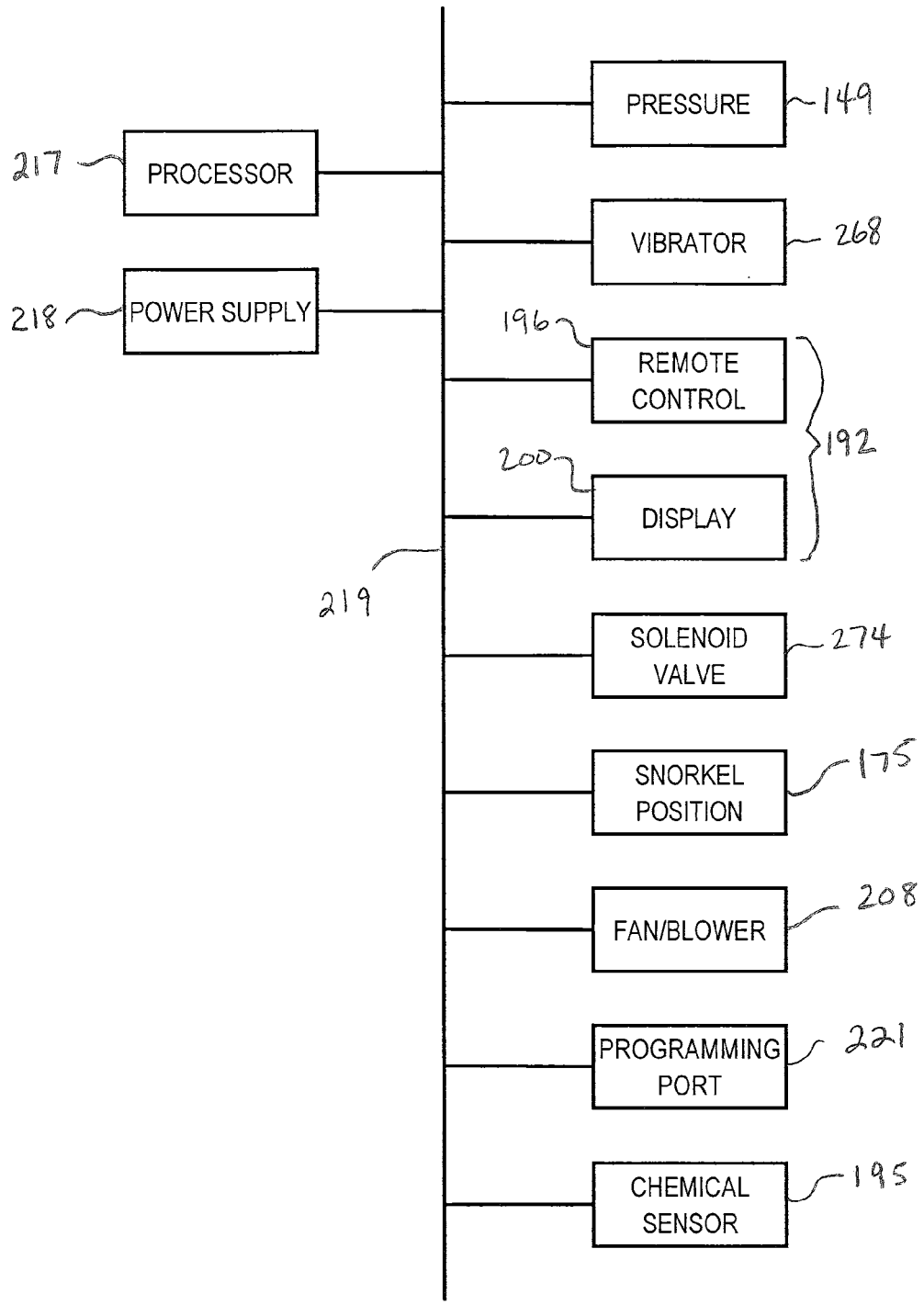
FIG. 15 is a schematic functional block diagram of a breathing system according to an exemplary embodiment of the present invention.
Figure 16:
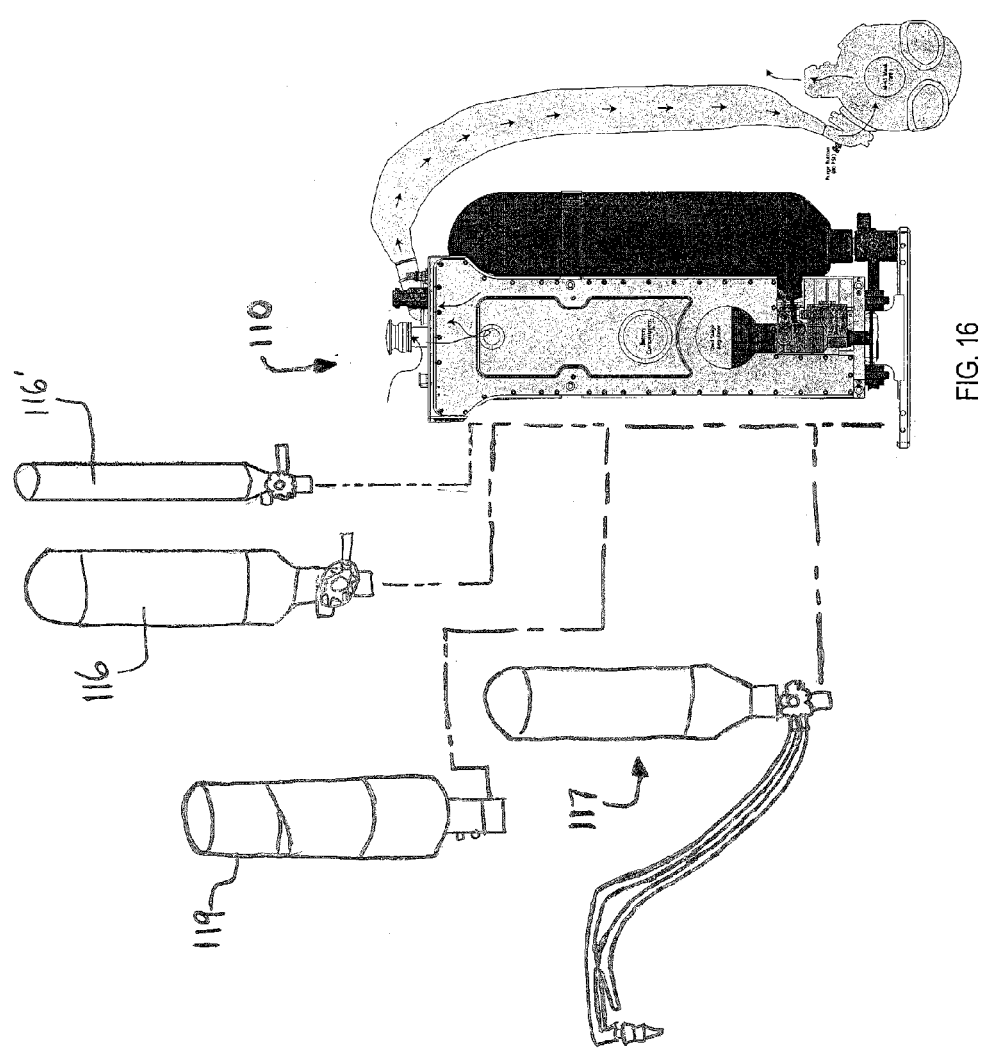
FIG. 16 illustrates the modular nature of the system and some exemplary modules which may be attached in place of one or both of the breathing gas cylinders to expand the functionality of the system.

The circuit board 214 may include a microprocessor, microcontroller, or other logic device 217, which is coupled via an electrical and/or data bus 219 to various system components, whereby various system components and parameters may be monitored and/or controlled (see FIG. 15). A programming port 221, such as a serial or parallel data interface port, may be provided on the chassis 112 for programming, updating, or testing the processing circuitry 217 (including an associated memory thereof) without the need to open the unit.

A removable housing cover plate or shell 115 encloses the internal components within the chassis housing 112 and is provided with an environmental seal or gasket to prevent air leakage out of the chassis and to prevent entry of moisture, debris, or environmental contamination therein. In a preferred embodiment, a cover plate is fastened to the first shell portion via a plurality of fasteners 117, such as threaded connectors, spaced about the periphery of the opening.

In the self-contained or pressurized mode of operation, breathing gas, typically air or oxygen, is stored under pressure in the one or more tanks or cylinders 116 that can be removably mounted to the housing section 112. The gas storage tanks 116 may be of any type suitable for supplying a breathing gas. The housing section may be adapted to accommodate tanks 116 of various, interchangeable sizes. For example, it may be desirable to select a tank size commensurate with the scope of an operation or mission, to employ smaller tanks in order to reduce the weight of the system, etc. Although the breathing gas will be described primarily in reference to compressed air for ease of exposition, it will be recognized that other suitable breathing gasses may be used as well. For example, in certain embodiments, one tank may contain compressed air while the other tank may contain oxygen. In this example, the tank containing oxygen would be designed to prevent oxygen flow into the system, the oxygen being used for an accessory function such as for use with a torch cutting 117 attachment.

In another preferred aspect, the tank 116 is suitable for high-pressure air/gas storage (e.g., up to about 9,500 PSI, or higher), and may be an aluminum-lined, composite (e.g., carbon fiber composite) wrapped high-pressure storage tank.

A modular system may be provided wherein one or more modules for expanding the functionality of the system may be attached to the chassis 112. Since the apparatus 110 may be operated with one or two tanks 116, or, in filtered mode, with no tanks 116, one or more special purpose modules may be provided which are interchangeable with one of the breathing gas cylinders 116.

In one embodiment, a cutting torch module 117 is contemplated. The cutting torch module may be of a type employing a burning metal, such as magnesium, a source of oxygen or other oxidizing gas, and a feed line for delivering the oxidizing gas to the surface of the material to be cut. The oxidizing gas is contained in a cylinder adapted to replace one of the breathing gas tanks 116.

In another embodiment, a heating and/or cooling module 119 is contemplated, wherein a circulating source of heating and/or cooling fluid, comprising a pump and a cooling source, heating source, or both, are provided in a module, e.g., a generally cylindrical module, adapted to mount in place of one of the breathing gas tanks 116. The heating/cooling module is adapted for use in connection with a tube-lined garment through which the fluid is circulated to effect heat exchange with the user's body and, preferably, may be electrically coupled to the power supply of the apparatus 110.

In still another embodiment, a hydration module may be provided, including a container adapted to be exchanged with a breathing gas tank 116 for supplying water or other suitable fluid to the user 128. Also, an alternatively sized cylinder 116' may be used in place of the cylinder 116.

The base manifold section 114 of the main system body 112 provides a platform for mounting the tanks 116. The base portion 114 includes a channel or opening 130. Likewise, the cylinder 116 includes a connection assembly 132 having a connection foot 134 adapted to be removably received in the opening 130. The connection foot is of complimentary size and shape (e.g., dovetail, tenon, or other geometrical configuration) with respect to the opening 130.

A fastener for removably retaining the tank 116 on the base section 114, such as a locking pin engaging aligned receiving holes on the base portion 114 and the connection assembly 132, or the like, may be employed. As shown in the illustrated embodiment, a locking pin 152 passing through a selected receiving hole 154 or 156 (e.g., depending on the size of the tank 116 employed) may be used to secure the cylinder foot 134 within the opening 130 and to prevent inadvertent ejection of the cylinder 116. The manifold connection assembly 132 may also include a pressure gauge 148 and a cylinder valve 150, e.g., a manually operable valve. In the depicted embodiment, the pressure gauges 148 face outward from the operator and may be viewed from the side of the device. The cylinder valves allow the operator to open and close the air flow from the cylinders 116 to an inlet 139 of manifold 140.

In the depicted embodiment, the connection assembly 132 may be adapted for either left-side or right-side mounting of the tank 116. A blow-out disk assembly 136 may be provided to relieve pressure in the event that cylinder pressure exceeds some prespecified value according to the tank capacity. In the event of excessive pressure, the burst disk will rupture. A pressure release cap 137 may be provided to retain the disk while pressure is released through the cap. The burst assembly 136 may include a blowout disk, O-ring and safety cap, providing the main pressure relief for the cylinders 116. When the disk blows, it opens an air escape path, allowing air to pass through the aerated cap 137. This prevents accidental damage to equipment and operator. In the depicted preferred embodiment, the burst assembly 136 faces away from the direction of an operator donning the apparatus 110.

The connection assembly 132 additionally includes a manifold connector 138 for providing an airflow connection to a manifold inlet 139 on the base portion 114. The connector 138 is preferably a threaded connector which is removably connected via complimentary threads on the inlet 139. A sealing ring or gasket, e.g., formed of a material such as a teflon or other sealing material, is preferably provided to provide a sealing engagement between the connector 138 and the inlet 140. The connectors 138 may include holes 141 or other features which provide for engaging a tool or key to provide leverage when rotating the connectors to ensure a tight fit.

The manifold connection assembly 132 additionally includes a fastener for securing the air cylinder 116 to the main body portion 112. The illustrated embodiment includes a retaining band 142 and one or more retaining nuts 144, e.g., which may be secured to the main body portion 112 to provide stabilization of the air cylinders on the main chassis. A screw-tight fastener 146 is provided for tightening of the band 142.

Figure 6:
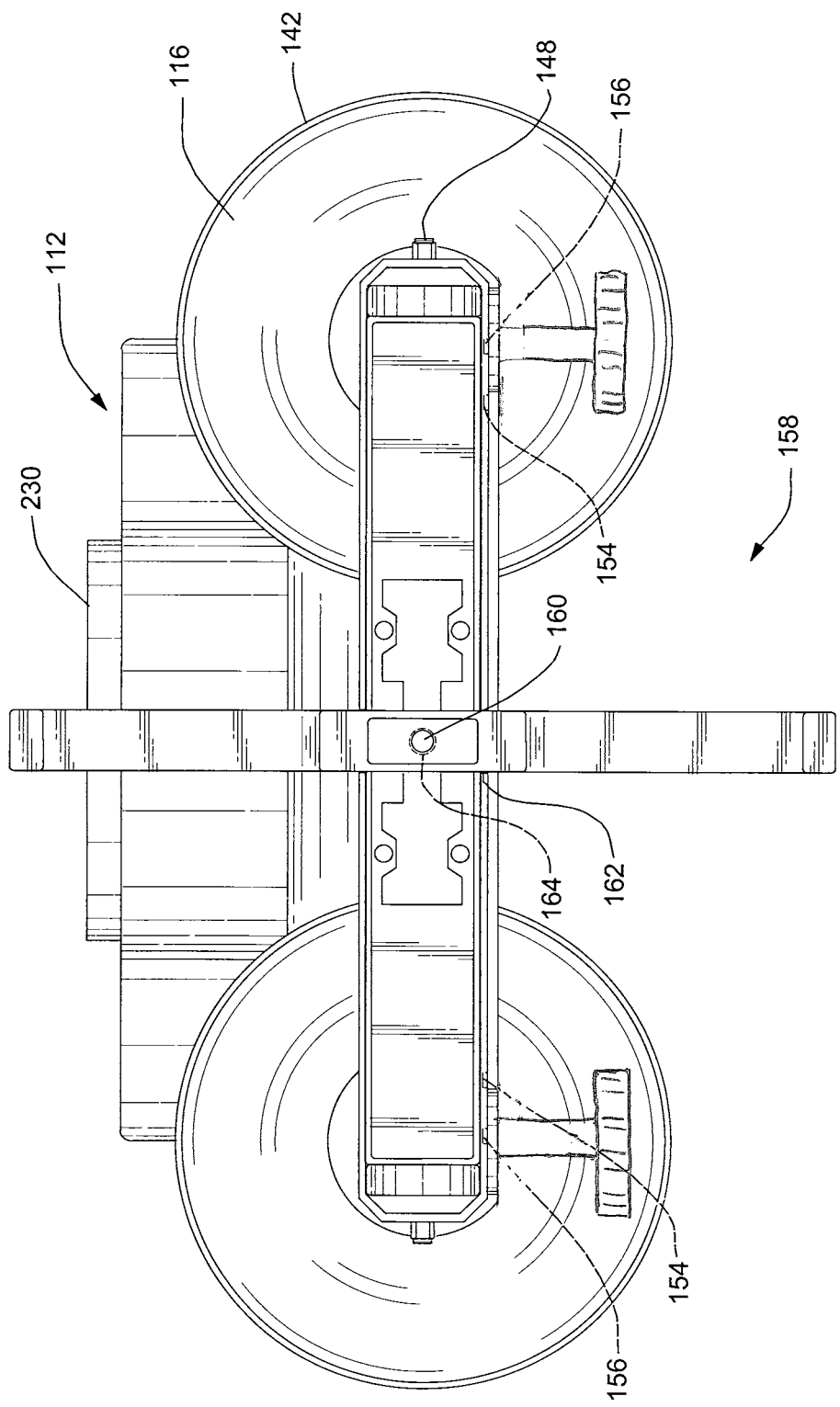
FIG. 6 is a bottom plan view of the breathing apparatus shown in FIG. 1.
Figure 7:
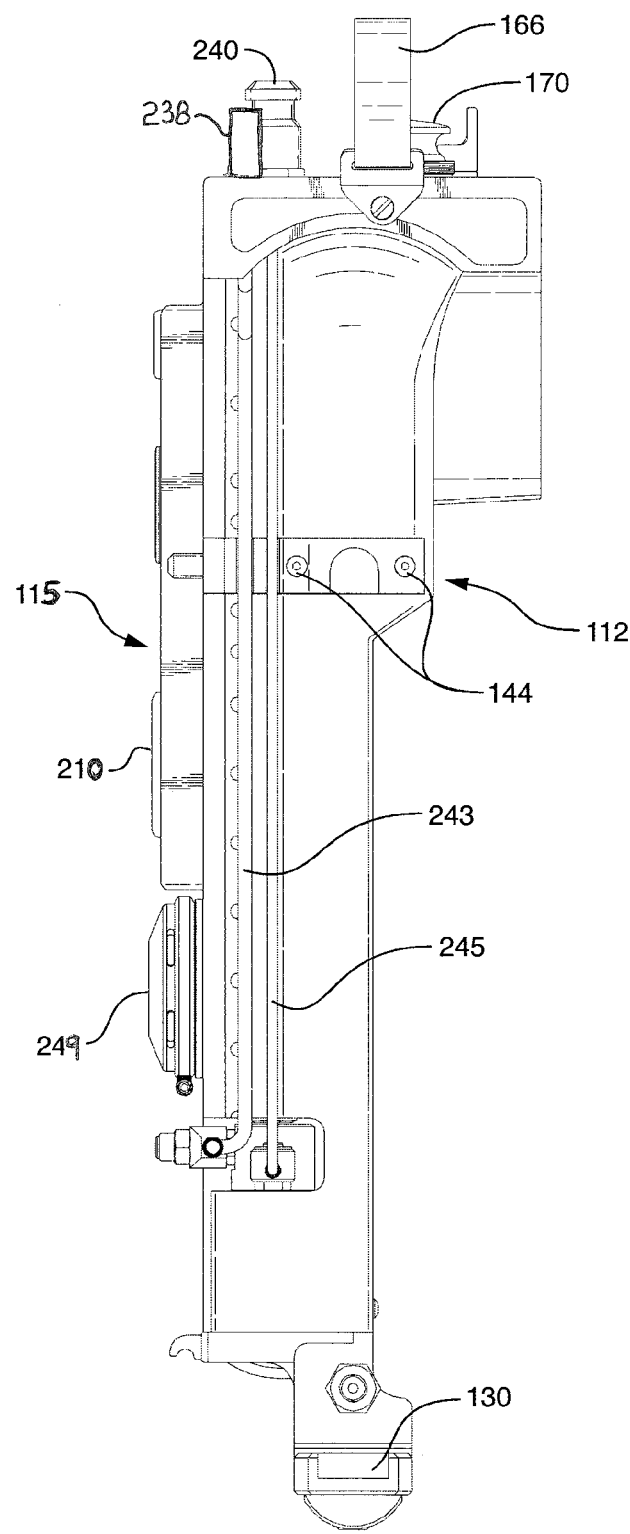
FIG. 7 is a side elevational view of the breathing apparatus with the tanks removed.

A retractable stand 158 may also be provided. In the illustrated embodiment, the retractable stand 158 pivots about a pivot pin 160. As best seen in FIG. 6, the stand 158 rotates between a first, retracted position (see FIG. 1) and a second, extended position (FIG. 6) for standing the unit 110 upright, e.g., for service or maintenance. In the illustrated embodiment, a notch 162 is provided in the base portion 114 for receiving the stand 158 when fully retracted. The stand is removably retained in the notch 162 by a captured spring 164. A handle or strap 166 is provided on an upper portion of the housing section 112 for carrying the unit 110 when it is not being worn. A hardened plastic storage case, which may include a foam lining, may be provided for storage of the unit 110 and its components when not in use.

Switching between the pressurized and filtration modes of operation is accomplished by a port valve for selectively receiving pressurized air or filtered ambient air. The port valve is controlled by a snorkel assembly 168 including a snorkel cap 170, an ambient air inlet 172, an optional prefilter 174, and a snorkel tube 176. The snorkel cap 170 is movable between a first, closed position (see FIG. 9) wherein the inlet 172 is closed to ambient air 178, and a second, open position (see FIG. 10) wherein the inlet may receive ambient air.

Figure 11:
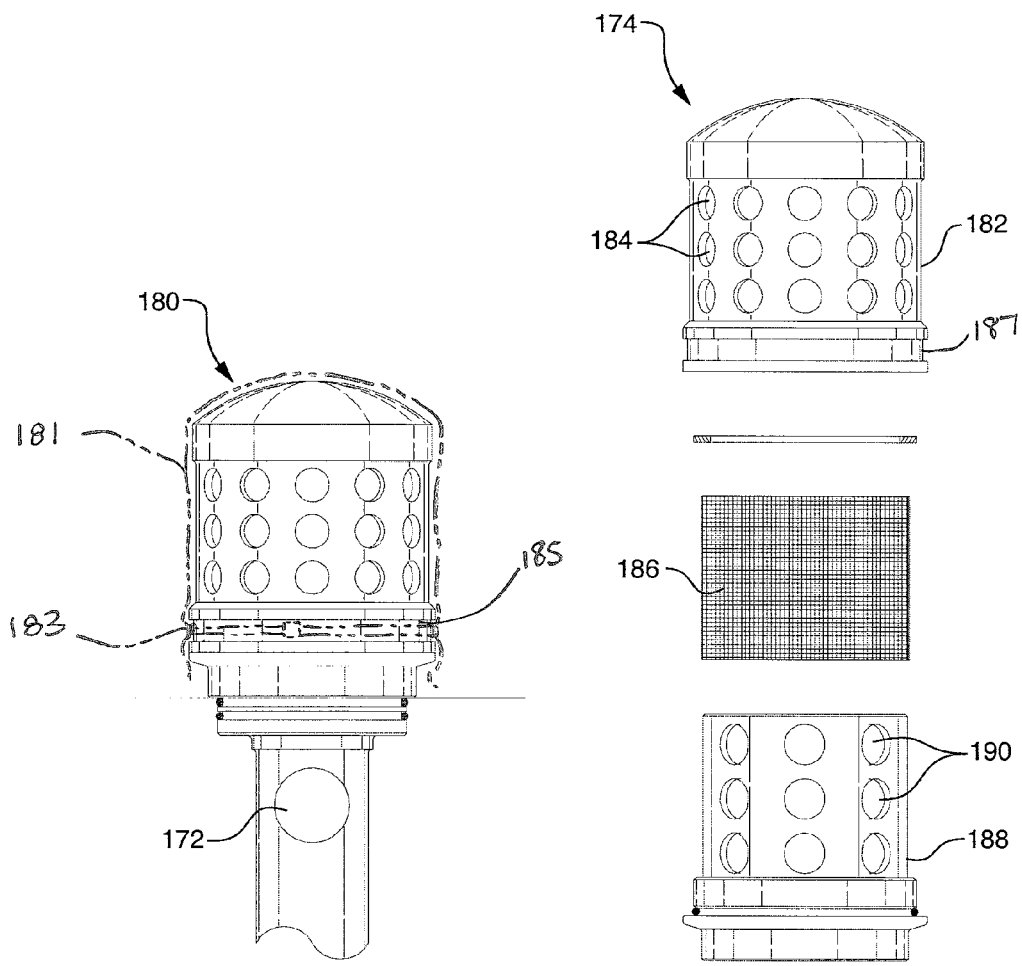
FIG. 11 depicts an exemplary, optional prefilter assembly.
Figure 12:
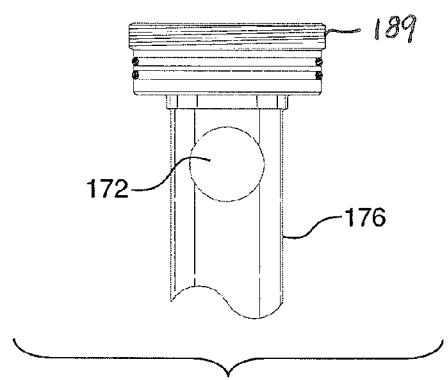
FIG. 12 is an exploded view of the prefilter assembly shown in FIG. 11.

An exemplary optional prefilter assembly 174 is shown in FIGS. 11 and 12. The prefilter assembly 174 includes a filter cap 182 and a filter housing 188, which houses a pre-filter filtration medium 186. The pre-filter medium 186 may be, for example, a polymeric material, such as polypropylene, polytetrafluoroethylene, or the like, and may be formed of a mesh material. In a preferred embodiment, the pre-filter material 186 is formed of a monofilament polypropylene mesh material. In a preferred embodiment, the prefilter 174 filters particles which are 10 microns in size or larger. The filter cap 182 and filter housing 188 include perforations 184 and 190, respectively, for passage of ambient air therethrough.

The optional prefilter advantageously provides filtering of ambient air prior to entry into the system, preventing dust buildup in the filter compartment chamber. The filter may be housed within a hardened housing 182 that has openings 184 formed therein and a connector, such as a threaded connector 189. This hardened cover protects the snorkel assembly from entanglement and other damage. A source of gas may be provided to unclog or remove dust and debris from the externally facing surface of the prefilter and/or main filter. That is, air or other gas may be passed air from an internal source outwardly therethrough, in the direction opposite to the air flow in normal, breathing operation. The source of gas may be, for example, the air contained in the breathing tanks 116, e.g., delivered from the first stage gas pressure regulator 244, via the connector 238, and so forth. Alternatively, or in addition, the source of the gas used for cleaning the filter may be a specially provided source, such as a carbon dioxide tank or cartridge. A valve and actuating means such as a manual valve actuator may be provided to allow the filter cleaning gas to be forced outwardly through the filter in quick bursts. Additionally, or alternatively, a burst of air may be forced outwardly through the prefilter each time the snorkel is raised prior to use. The burst of air may be actuated, for example, via a switch or other snorkel position indicator 175 (see FIG. 15) located on the prefilter cap or elsewhere on the prefilter assembly. The switch may be, for example, an electrical switch or position indicator providing a signal for actuating or controlling an electrically operated air valve, a mechanical air valve actuator, and so forth. The burst of air may be actuated under preprogrammed control whenever the snorkel is moved from closed to open position.

In the depicted preferred embodiment, the housing 182 is adapted to accommodate an additional, external filter 181. The filter comprises a mesh or woven filtration medium which covers the cap 182 and perforation 184 and is secured at the base with an annular fastener 185 such as a tie, band or the like. Advantageously, a groove 187 is provided to prevent the flow of air around the external filter 181 and to prevent dislodging of the annular fastener 185. In a preferred embodiment the external snorkel filter 181 is formed of a woven nylon material of a type used for nylon hosiery. The external filter 181 is readily cleaned or replaced and prolongs the life of the inner filtration medium 186.

The snorkel assembly may be moved between the open and closed positions by manually lifting or depressing the snorkel cap 170, respectively. Alternatively, a control module 192 may be provided for switching between pressurized tank air and filtered air. The control module includes a housing 194, a button or key 196 for toggling between the filtered and self-contained air sources, a visual indication or display 198 indicating the air source currently selected and a display 200, such as a liquid crystal display (LCD), light emitting diode (LED) display, or the like, indicating the system pressure or pressure remaining in the tank 116. The control module 192 may also control and/or display blower motor speed, cylinder pressures, battery life, friend/foe identification system, or the like. It may also contain a backlight for the display 200.

It will be recognized that alternative configurations of the control module 192 may also be employed. For example, a single display combining the pressure display 200 and the source selection indicia 198 may be used.

An electrical cable 202 electrically couples the module 192 to the electrical system of the apparatus 110, e.g., via an electrical connector 204 which may be connected to a mating electrical connector 206 on the housing 112. The connectors 204 and 206 may include mating threaded connector housing members. The button 196 also serves to activate an internal suction source 208, such as a fan or blower (the terms "fan" and "blower" will be used interchangeably herein unless specifically stated otherwise) via the electrical cable 202 when filtered ambient air is selected as the air source.

Optionally, programming or control circuitry in the apparatus 110 may be provided to automatically switch from pressurized mode to filtered mode when the remaining air supply in the tank 116 is exhausted or substantially exhausted, or the tank pressure or system pressure otherwise falls below preselected value.

The main housing portion 112 further includes a battery compartment 210 containing a power supply 218, such as one or more batteries or battery packs for providing power to the electrical components of the apparatus 110. In some cases, the power supply 218 may also electrically coupled to provide power to one or more electrically operated, externally mounted modules which may be provided to expand the functionality of the apparatus 110. In the depicted embodiment, a removable cover 212 is provided on an exterior surface of the housing portion 112, and is preferably sealed against moisture and other external contaminants, e.g., via an O-ring or other sealing ring or gasket. In the illustrated embodiment, a power selection switch 216 is provided on the battery compartment cover 212 for turning the device 110 on and off. When turned on, the power system powers the blower, control module, and any other electrical components, such as a pressure sensing and alert system (as described in greater detail below), or other optional chassis-mounted components.

In a preferred embodiment, the compartment 210 accommodates eight 3-volt batteries, such as lithium ion batteries, in which four chambers each accommodating two batteries in series configuration and the four chambers being electrically connected in parallel. Thus, in this preferred embodiment, the compartment thus accommodates up to four sets of two batteries to provide a 6-volt output. In this manner, the unit may be operated on fewer than eight batteries for noncritical applications, such as training, testing, or servicing of the apparatus, whereas a full complement of eight batteries is recommended for a full mission. It will be recognized that other battery and battery compartment configurations, including removable and/or rechargeable batteries or battery packs, and the like can be used. Likewise, an external electrical connector may also be provided for recharging the internal batteries when a rechargeable power source is used.

A main filter compartment 220 in the chassis 112 houses a main filter 222, such as a radiological, biological, or chemical filter. The filter 222 includes an inlet 224 for receiving ambient air 178, which may be prefiltered in the case wherein an optional prefilter is employed. The filter 222 further includes an outlet 226 for filtered air.

The filter 222 is preferably secured within the compartment 220 via a connector 228. Preferably the connector 228 is a threaded connector, most preferably a standard NATO 55-millimeter male threaded connector which removably rotatably engages a complimentary female threaded connector in the compartment 220. An O-ring or other sealing ring or gasket 229 is provided in the base of the threaded connector to prevent flow around the filter canister 222. A filter compartment cover 230 seals against air leakage and against the entry of moisture or other contaminants. The filter cover may be formed of aluminum and include threads which rotatably and removably engage complimentary threads formed in the filter compartment 220. An O-ring 231 or other sealing ring, gasket, or the like, may be provided to provide an environmental seal. In a preferred embodiment, an extension ring or sleeve may be provided between the compartment 220 and the cover 230 to extend the compartment and accommodate additional filter sizes. Because the filter compartment 220 is not exposed to air when the snorkel is down, the apparatus 110 allows for extended storage of the filter 222 without degradation due to exposure to air. In this manner, the filter may be installed in advance of use, thereby improving response time as compared to a conventional PAPR unit in which the filters must remain in a separate sealed container or packaging and installed just prior to use. Likewise, the apparatus 110 may be used in SCBA mode in rain or other wet conditions, including under water, without affecting the filter.

An intermediate-pressure "buddy" connector 238 may be provided on an exterior surface of the chassis 112 and is preferably of a quick connect/disconnect type as generally know in the art. The connector 238 is in flow communication with the first stage regulator 244 via conduit 243 and provides an external (e.g., about 80 psi) connection for attaching various second stage regulators. In this manner, use of the air supply of the breathing system 110 may be shared by attaching an external breathing device or mask incorporating a second stage regulator. Alternatively, the intermediate pressure connection port 238 may be used to operate pneumatically operated tools and devices. A connection cap 239 may be provided to prevent moisture and debris from contaminating the connection 238.

A high-pressure charging valve 240 may be provided on an exterior surface of the chassis 112 for connection with an external charging device for charging the tanks 116 with air/breathing gas. The valve 240 is in flow communication with the manifold 140 via conduit 245. A protective cap 241 may be provided to prevent moisture and debris from contaminating the connector 240. The connector 240 is preferably of a quick connect/disconnect type as generally known in the art. In addition to charging the tanks 116, the high pressure port 240 may also be used to couple the apparatus 110 to an external source of breathing gas. The external source may be, for example, an additional tank or may be a stationary source of breathing gas, e.g., a compressor or a pressurized vessel, in which case the user is tethered to the stationary breathing gas supply by a line connecting the connector port 240 and an outlet of the source.

In operation, one or both of the cylinder valves 150 may be opened and the connector 240 connected to a source of breathing gas and charged to a desired pressure. The cylinder valves 150 may then be closed and the charging source disconnected from the connector 240.

The chassis 112 additionally includes at least one connection port (122, 123) for connection to the breathing hose 118. In the depicted embodiment, left-side and right-side connection ports 122 and 123, respectively, are provided to accommodate both left-handed and right-handed operation. For example, the left port 122 provides a left-side connection for the breathing hose 118, thereby keeping the right side free for a right-handed marksman. Likewise, the right port 123 provides a right-side connection for the breathing hose 118, thereby keeping the left side free for a left-handed marksman.

Figures 13, 14:
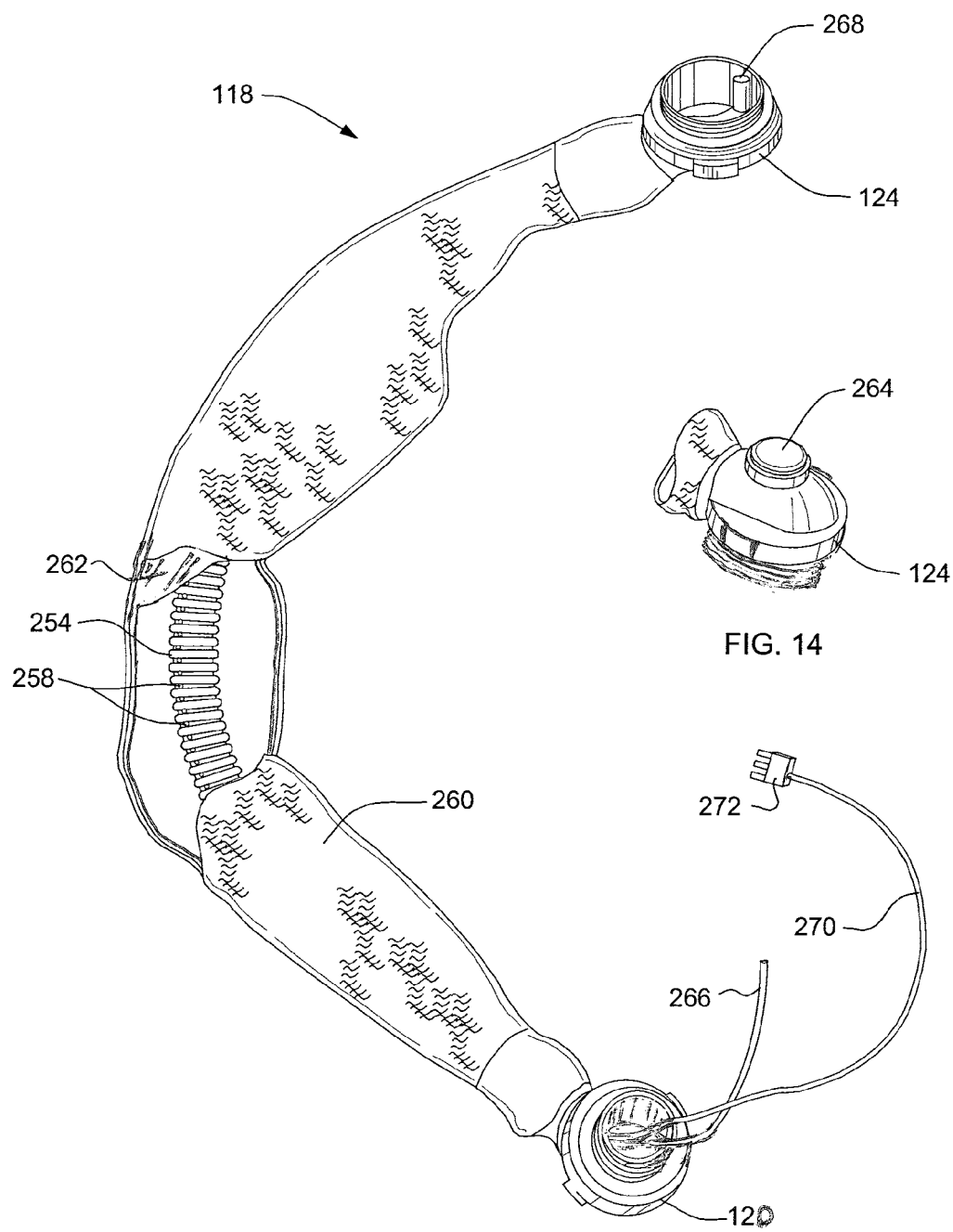
FIG. 13 illustrates an exemplary breathing hose according to a preferred embodiment having a vibrator alarm and purge valve.
FIG. 14 illustrates the purge valve on the mask connector end of the breathing hose shown in FIG. 13.

The breathing hose 118 is attached to a selected one of the ports 122 and 123 via the hose connecting end 120. A blanking plug or cap 242 seals the other one of the ports 122 and 123 to prevent contaminant entry via the unused port. The connection between the ports (122, 123) and the hose connector end 120 or the plug 242 are preferably of a quick connect/disconnect type and preferably incorporates an O-ring or other sealing ring or gasket to seal against entry of moisture or other external contaminants. The port readily accepts the quick-connect end of the breathing hose, and contains a quick-connect electrical appliance for powering the vibrator unit within the mask adapter and a gas line for coupling to the purge valve line 266 (see FIG. 13) in breathing hose 118.

In the pressurized mode of operation, the snorkel is in the down or closed position and one or both of the valves 150 are opened. Air exits the cylinders 116 via the respective open valve 150 and passes the pressure gauge 148 and pressure relief assembly and enters the main manifold 140 of the housing 112.

The air then passes to a first stage regulator 244, which may be of a type commonly used for pressurized or self-contained breathing apparatuses. The first stage regulator 244 may be of a type, for example, including a diaphragm which is acted upon by fluid pressure to reduce the pressure of the air passing through the regulator. The pressure is reduced to a first reduced pressure level, which is preferably about 80-100 psi. The first stage regulator 244 may also include a relief valve for pressure relief for the regulator when the pressure of the gas exiting the first stage regulator exceeds some pre-selected or pre-determined value, e.g., about 100-120 psi. The relief valve may be, for example, of a spring-loaded type which relieves pressure at a first threshold value and returns at a second threshold level. For example, the relief valve may relieve at a pressure of about 100-120 psi and return at a pressure of about 90-110 psi.

Air then passes from the first stage regulator 244 to a regulated pressure junction 246 and on to a second stage regulator 248 where it is further reduced for breathing. In addition to supplying the breathing gas to the second stage regulator 248, the regulated pressure junction 246 may also divert gas at about 80 PSI to additional locations within the breathing apparatus 110 for various pressure actuated services as described herein, such as an optional purge valve, a gas driven piston for selecting between the self-contained and filtered modes of operation, air for prefilter cleaning. The second stage regulator 248 reduces the air pressure to a level suitable for safe breathing (e.g., about 1-5 psi). Air passing through the second stage regulator 248 is then delivered to the operator via the compartment 113 and the hose 118 to the interior of the mask assembly 126.

In the depicted preferred embodiment, air passes from the second stage regulator 248 through a conduit 250 to an internal orifice 252 then into the chassis 112, the inside of which is a compartment defining an internal breathing air reservoir or chamber 113.

An outlet valve 127 on the mask 126 includes a one-way check valve placed over the existing breathing exhaust port on the face mask through which gas in the mask 126 may exit in the event the pressure in the mask is above some threshold level. The pressure of the gas in the mask, either from the suction source 208 or from the second stage gas pressure regulator 248, is greater than the ambient, atmospheric pressure, thereby resisting entry of external air, even in the event that the seal between the user's face and the mask is momentarily broken, e.g., due to user movement. This positive pressure in the mask also assists in preventing fogging of the interior of the mask.

Figure 17:
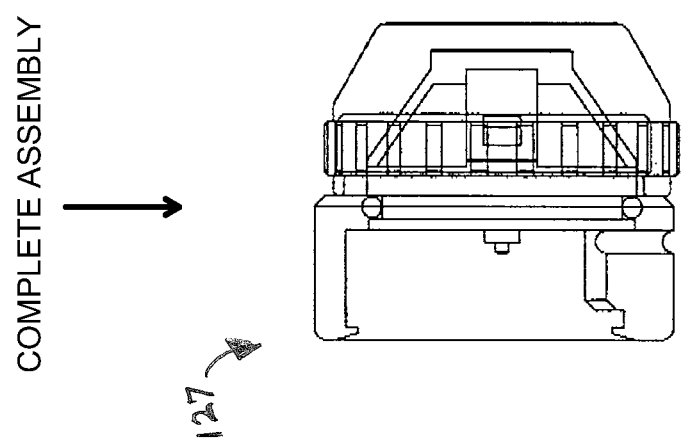
FIGS. 17 and 18 are assembled and exploded views, respectively, of a one-way check valve for attachment to a port of the user's face mask.
Figure 18:
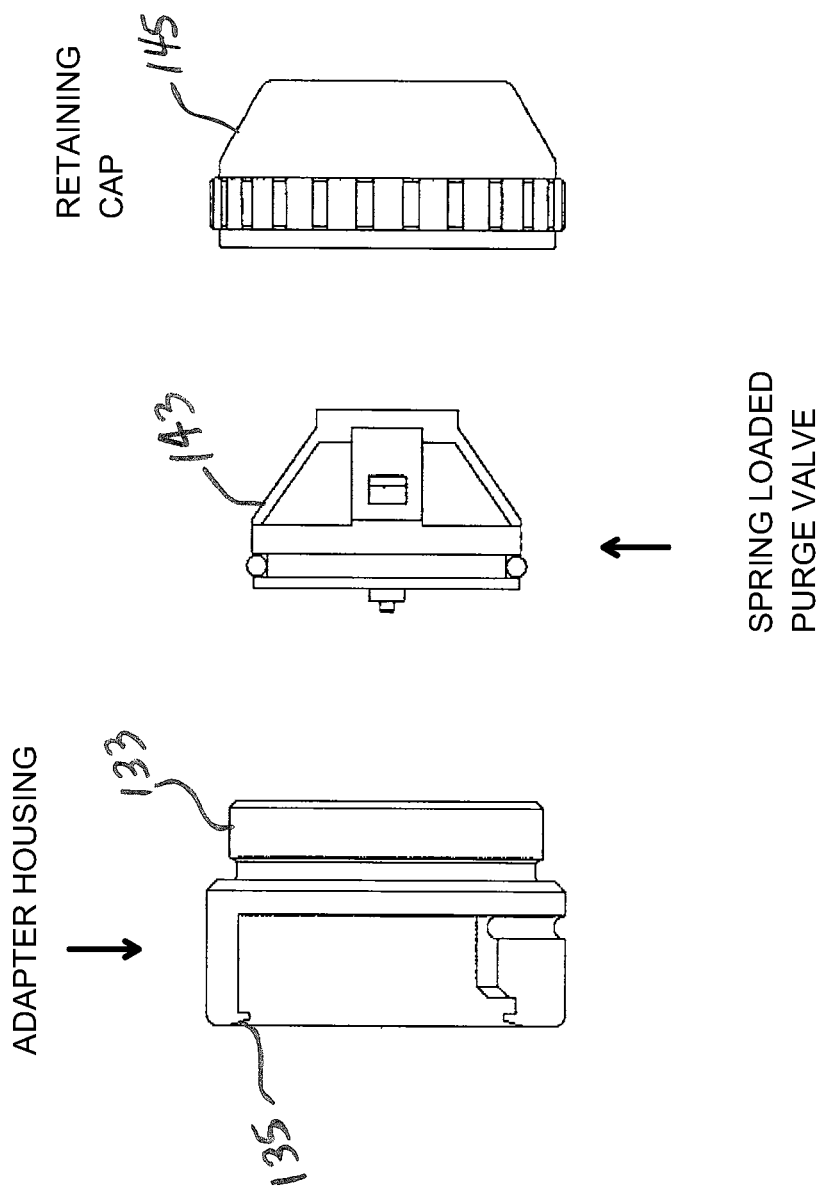

The outlet valve 127 is shown in FIGS. 17 and 18. The device is placed over the existing breathing exhaust port on a protective mask. It may be fastened in place via an adapter housing 133 with adhesive and a mechanical hook system 135 which mates with the adapter port on the mask. The device includes a spring-loaded outlet valve 143 regulates exhaust air flow by use of a calibrated spring that provides compression on the purge valve. The purge valve is retained via an annular retaining cap 145. The valve 143 may be made of various materials including polymers and may be coated with HSF, PTFE, or the like. The outlet valve 127 maintains regulated positive pressure in the mask thus eliminating the free flow of air, or other breathable gas, from the mask's standard exhaust port. The outlet valve 127 is also designed so that it releases gas from inside the mask before the pressure inside the mask is raised to the point where gas is exhausted between the mask's sealing surfaces and the wearer's skin. Breaking the seal between the mask's sealing surface and the wearer is not a desired occurrence because of the probability of introducing a contaminant into the mask thus incapacitating the wearer. In the event that the mask seal is inadvertently breached the positive pressure created by the mask adapter 127 eliminates the possibility of a contaminant entering the mask.

Preferably, the second stage regulator 248 includes a diaphragm responsive to pressure differentials to provide demand breathing gas to a user in communication with the regulator 248. Air in the chassis 113 is held in place until demand is placed on the system, i.e., when the operator inhales. Air then passes through the outlet (122, 123) of the internal chamber 113 through the hose 118 connecting the main system body to the mask.

In certain embodiments, the exterior facing surface of the diaphragm may be coated or treated to protect against corrosion or degradation when exposed to chemical or biological agents. In one embodiment, a protective polymer layer is bonded to or deposited on the outward surface of the diaphragm. The polymer layer is preferably a polymer having a high degree of chemical resistance such as a fluorine-containing polymer and, more preferably, polytetrafluoroethylene (PTFE). The polymer layer may be applied in the form of a sheet or film bonded to the diaphragm or in the form of a solution or dispersion, e.g., liquid, paste, cream, gel, or similar formulation, containing monomers and/or polymer precursors, which are subsequently cured in place to form the protective layer. A removable cover or port 249, secured by a retaining ring or clamp 247 may be provided to allow access to or servicing of the second stage regulator diaphragm.

Other components may also be provided with a protective polymer layer to prevent degradation in harsh chemical and/or biological environments as described above and in one embodiment, the entire assembled unit may be coated with a solution or dispersion of monomers and/or polymer precursors and cured to protective polymer film, preferably of PTFE, over the entire unit prior to use.

Any known type of breathing hose may be employed as the breathing hose 118. However, in a preferred aspect, an inhalation hose assembly providing next breath capability is provided. In the depicted exemplary embodiment shown in FIGS. 13 and 14, the illustrated inhalation hose assembly 118 includes an inner perforated hose 254 having perforations 258 along its length, which is contained within a flexible outer bag 260. The outer bag inflates to provide a ready volume of air, e.g., up to two liters of air, providing the operator with a "next breath" capability. The additional volume of air contained in the bag 260 is especially advantageous in that it eliminates the need for employing multiple filters and blowers in that sufficient volume of breathing gas is delivered to the user, even under high exertion. The "next breath" capability also provides positive pressure (e.g., about 5 psi) in the user mask 126. The inner hose 254 also provided a structural strengthening between the ends of the hose 118 and serves to house the electrical cable 270 and purge line 266.

The bag 260 may be formed of a woven polymeric material, such as a high strength fluoropolymer (HSF), polytetrafluoroethylene (e.g., Teflon), etc. Optionally, an inner lining 262 may also be disposed between the perforated hose and the outer bag. The inner lining or bag 262 may be formed of a natural or synthetic polymer material, such as butyl rubber or the like. The optional inner lining 262 functions as a bladder and provides an extra level of protection against external contaminant entry into the air stream, e.g., in the event the outer bag 260 is cut or abraded. A fire-retardant layer or coating may also be provided or applied to the bag 260.

The inhalation hose assembly 118 is connected to the chassis portion 112 via the connector 120 and to the user mask 126 via a connector at 124 at the proximal end of the hose 118. The connectors 120 and 124, which may be the same or different, may be, for example, threaded connectors, quick-connect type connectors (e.g., having one or more resilient protrusions engaging a depression), and the like. Also, one or more sealing rings or gaskets (not shown) may be provided to prevent moisture and other contaminant entry into the system. As described above, the preferred depicted embodiment accommodates connection of the hose 118 on either side of the chassis 112, according to the user's preference. In another preferred aspect, the connectors 120 and/or 124 may be adapted to swivel or rotate to accommodate user movement, to switch between right and left-handed operation.

In the depicted embodiment, the hose assembly 118 includes an optional purge valve 264 that provides the operator with an additional burst of regulated air from the first stage regulator 244 (e.g., about 80-100 psi) when needed. The purge valve assembly 264 can include a manually controlled actuator and connection hose 266 that is in fluid communication with the first stage regulator 244 in the main body portion 112 for introducing additional air into the user mask. The connection hose 266 preferably passes through an interior portion of the hose assembly 118 and, more preferably, through an interior portion of the perforated inner hose 254. In the depicted embodiment, the hose 266 extends through the end 120 of the hose 118, allowing connection to a mating connector within the selected connection port 122 or 123. Gas is delivered from the first stage regulator 244 via the regulated pressure junction 246.

Another optional feature of the system is to provide a user perceptible alert when the air pressure drops below a preselected pressure level (e.g., below 500 PSI). Such alert may be a visual or audible alarm or, more preferably, a vibrating mechanism that alerts the user without drawing attention to the user. Preferably, the pressure detected is system or manifold pressure, although employing tank pressure is also contemplated. For example, an electronic pressure gauge or electronic transducer 149 (see FIG. 15) may be housed within the manifold 140.

The vibrator 268 or other alarm mechanism may be mounted within the inhalation hose assembly 118, preferably in or near the mask connection end 124. The vibrator 268 may be electrically coupled to the main power source within the main body portion 112, e.g., by means of an electrical connection 270 passing through the inhalation hose assembly 118 and, preferably, within the perforated hose 254. The electrical coupling 270 may include a connector 272 which mates with a corresponding connector allowing connection to a mating connector within the selected connection port 122 or 123. Alternatively, a dedicated power supply, such as a battery or battery pack, for the vibrator or other alarm 268 is also contemplated.

The vibrational unit 268 may employ any of a number of generally known vibrational elements for producing mechanical vibrations. For example, the vibrational element may employ an electric motor wherein a pivotally mounted weight is mounted at the end of the shaft thereof. Alternatively, other vibrational elements may be utilized to produce mechanical vibrations, such as a piezoelectric substance (e.g., quartz, Rochelle salts, or various artificial materials). The application of an electrical signal to the piezoelectric material induces the material to mechanically vibrate.

It will be recognized that the electrical supply 270 passing through the hose 118 may also be employed to power one or more additional devices in the mask. For example, the power supply cable 270 may be employed to provide power to a display device, such as a head up display, indicator lights, a communication system, and so forth, which may be mounted or integrated with the user mask.

Referring now to the blower-assisted filter mode of operation, the snorkel assembly 168 is moved to the open position, e.g., either electronically or manually, as described above. When controlled electrically, an electronically actuated solenoid valve 274 releases pressurized air from the first stage regulator 244 to close the orifice 252 in the snorkel. The snorkel assembly is urged to the open position via a mechanical linkage 281 between a cylinder/piston assembly 280 and the snorkel assembly 168 to open a filtered air valve inlet 276.

In the depicted embodiment, pressurized air from the first stage regulator 244 is in fluid communication with the gas-driven piston/cylinder assembly 280, which controls the movement of the snorkel using the 80 PSI air that comes from the regulated pressure junction 246. An electronic sensor controls the flow of gas to the piston/cylinder assembly 280 when the operator presses the button 196 on the remote control unit 192. In the depicted embodiment, the piston/cylinder assembly 280 is fluidically coupled to the regulated pressure junction 246 via a conduit 282 when the solenoid valve 274 is opened. The piston assembly 280 is thereby extended and retracted to move the snorkel assembly to the open and closed positions, respectively, by the release of air from the first stage regulator 244. A removable cover 279 may be provided to allow access to the piston assembly 280 without the need to remove the entire cover 115.

A snorkel position sensor 175 such as a switch, position indicator, or the like, may be provided to provide an indication of snorkel position and/or for actuating a prefilter cleaning function as described above.

It will be recognized that other mechanisms for moving the snorkel between the open and closed positions. For example, an electric motor and a mechanical linkage for converting rotation of the motor into translation of the snorkel may be employed in place of the piston assembly 280.

However, it will be recognized that the unit 110 may be operated with one or both cylinders 116 removed from the main body 112. Cylinder manifold plugs may be secured over the manifold inlets to seal the manifold intake connections to prevent contaminant entry when the cylinders are not in use. When both cylinders 116 are removed, the snorkel assembly 170 may be manually moved to the open position in order to activate the suction source 208 and allow air to flow through the filter mechanism. It is also contemplated that a dedicated source of gas for operation of the piston assembly 280, such as a carbon dioxide tank or cartridge or the like be provided for operating the piston assembly 280.

In the open position, ambient air 178, e.g., possibly contaminated air, is drawn in by the suction source 208 through the through the inlet 172, optional prefilter 180, and main filter 222 as described above. Air passes through the filter and into the breathing reservoir 113 of the chassis housing 112. From there, the air flows into the user mask 126, e.g. via the inhalation hose assembly 118, as previously described.

Optionally, a connector 193 is provided for electrically coupling an optional air sensor module 195 (see FIG. 15) which samples and monitors the ambient air for harmful constituents which are unfilterable by the main filter 222. In one such embodiment, if the user is operating the apparatus in the filtered mode and such constituents are detected or the air quality is otherwise determined to be unsafe, the snorkel is moved to the closed position and switched to the self-contained mode of operation under preprogrammed control. An audible, visual, or tactual warning signal may also be provided to the user.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A breathing apparatus, comprising:
   a conduit defining a passageway for a breathable gas having a first inlet for receiving breathable gas from a pressurized source of breathing gas, a second inlet for receiving filtered ambient air, and an outlet for delivering breathable gas to a user;
   a suction source in fluid communication with said second inlet for drawing ambient air into said passageway;

a main filter assembly positioned between said second inlet and said passageway for removing contaminants from said ambient air;

a prefilter assembly positioned upstream of the main filter assembly, said prefilter assembly including one or more prefilter elements, said prefilter assembly including a prefilter housing receiving said one or more prefilter elements, said prefilter housing movable between a closed position wherein said second inlet is closed to ambient air and an open position wherein said second inlet is open to ambient air;

a pneumatically operated piston reciprocally movably within a cylinder, said piston mechanically coupled to said prefilter housing;

a normally closed passage extending between said cylinder and the pressurized source of breathing gas; and a valve for selectively opening said normally closed passage to deliver pressurized breathing gas to said cylinder, wherein when the prefilter housing is in the open position, the pressurized breathing gas delivered to the cylinder causes the prefilter housing to be moved to the closed position and wherein when the prefilter housing is in the closed position, the pressurized breathing gas delivered to the cylinder causes the prefilter housing to be moved to the open position.

2. The breathing apparatus of claim 1, further comprising:
a face mask adapted to be worn over a user's face and having a connection port; and
an air hose having a first end removably connected to said face mask connection port and a second end opposite the first end removably connected to said outlet.

3. The breathing apparatus of claim 2, further comprising one or both of:
a purge valve connected to said first end of said air hose, the purge valve fluidically connected to said first stage regulator and manually actutable to provide a burst of regulated air from a first stage regulator; and
an alarm system for providing a user-perceptible alert when a pressure of the self-contained breathing system falls below a preselected value.

4. The breathing apparatus of claim 2, wherein said air hose comprises an inner perforated hose for delivering air to a user and an outer flexible bag which is inflatable to hold a volume of air for subsequent delivery to the user.

5. The breathing apparatus of claim 1, wherein said one or more prefilter elements includes:
a first prefilter element formed of a woven nylon material; and
a second prefilter element formed of a mesh filtration medium.

6. The breathing apparatus of claim 5, wherein said mesh filtration medium is adapted to filter particles having a size of about 10 microns or larger from the ambient air.

7. The breathing apparatus of claim 1, further comprising:
one or more self-contained sources of breathing gas removably attached to said passageway and selectively fluidically coupled to said first inlet.

8. The breathing apparatus of claim 1, wherein said normally closed valve is a solenoid valve.

9. The breathing apparatus of claim 1, wherein said main filter assembly is positioned between said second inlet and said suction source.

10. The breathing apparatus of claim 1, wherein the passageway is sealed against entry of one or both of water and environmental contamination when the prefilter housing is closed.

11. The breathing apparatus of claim 1, further comprising:
an actuator for activating the suction source when the prefilter housing is in the second position and deactivating the suction source when the prefilter housing is in the first position.

12. The breathing apparatus of claim 1, further comprising:
a pressure sensor for detecting a pressure indicative of a quantity of gas remaining in the self-contained source of breathing gas; and
said valve operable under programmed control responsive to detected pressure reaching a preselected minimum threshold value.

13. The breathing apparatus of claim 1, further comprising:
a pressure regulator for receiving pressurized gas at a first pressure and outputting the gas at a second pressure lower than the first pressure;
said valve in fluid communication with said pressure regulator.

14. The breathing apparatus of claim 1, wherein the main filter assembly includes a main filter selected from a chemical, radiological, or biological filter, or any combination thereof.

15. The breathing apparatus of claim 1, further comprising:
said conduit defining a passageway including a housing defining an internal cavity, the internal cavity providing a reservoir of breathable gas.

16. A breathing apparatus, comprising:
a conduit defining a passageway for a breathable gas having a first inlet for receiving breathable gas from a pressurized source of breathing gas, a second inlet for receiving filtered ambient air, and an outlet for delivering breathable gas to a user;

a suction source in fluid communication with said second inlet for drawing ambient air into said passageway;

a main filter assembly positioned between said second inlet and said passageway for removing contaminants from said ambient air;

a prefilter assembly positioned upstream of and in series with the main filter assembly, said prefilter assembly including one or more prefilter elements configured to trap particles in ambient air drawn into said passageway before it flows to said main filter assembly, said prefilter assembly including a prefilter housing receiving said one or more prefilter elements, said prefilter housing movable between a closed position wherein said second inlet is closed to ambient air and an open position wherein said second inlet is open to ambient air;

a pneumatically operated piston reciprocally movably within a cylinder, said piston mechanically coupled to said prefilter housing;

a normally closed passage extending between said cylinder and the pressurized source of breathing gas; and a valve for selectively opening said normally closed passage to deliver pressurized breathing gas to said cylinder, wherein when the prefilter housing is in the open position, the pressurized breathing gas delivered to the cylinder causes the prefilter housing to be moved to the closed position and wherein when the prefilter housing is in the closed position, the pressurized breathing gas delivered to the cylinder causes the prefilter housing to be moved to the open position.

* * * * *